United States Patent [19]

Wade et al.

[11] 3,996,363
[45] Dec. 7, 1976

[54] 2-[(4-OXO-1-PHENYL-1,3,8-TRIAZAS-PIRO[4.5]DECAN-8-YL)ALKYL]-1H-BENZ-[DE]ISOQUINOLIN-1,3(2H)-DIONES

[75] Inventors: Peter C. Wade, Pennington, N.J.;
Berthold Richard Vogt, Yardley, Pa.

[73] Assignee: E. R. Squibb & Sons, Inc., Princeton, N.J.

[22] Filed: June 13, 1975

[21] Appl. No.: 586,678

[52] U.S. Cl. .................. 424/258; 260/281 NH; 260/281 SP; 260/281 S; 260/293.66
[51] Int. Cl.² ............. A61K 31/645; A61K 31/47; C07D 471/10; C07D 401/06
[58] Field of Search .......... 260/281 NH, 281 SP, 260/295 T, 295 K, 293.66, 281 S; 424/258

[56] References Cited

UNITED STATES PATENTS

| | | | |
|---|---|---|---|
| 3,155,669 | 11/1964 | Janssen | 260/294 |
| 3,155,670 | 11/1964 | Janssen | 260/294 |
| 3,161,644 | 12/1964 | Jannssen | 260/293 |
| 3,238,216 | 3/1966 | Janssen | 260/293.4 |
| 3,247,208 | 4/1966 | Schenker | 260/281 |
| 3,560,495 | 2/1971 | Frankus et al. | 260/247.1 |
| 3,625,947 | 12/1971 | Noguchi | 260/281 |
| 3,629,267 | 12/1971 | Kaiser | 260/295 K |
| 3,642,836 | 2/1972 | Cusic et al. | 260/281 |
| 3,759,927 | 9/1973 | Huebner | 260/293.58 |
| 3,770,763 | 11/1973 | Cusic et al. | 260/309 |
| 3,826,835 | 7/1974 | Huebner | 424/267 |
| 3,839,341 | 10/1974 | Scharpf | 260/293.66 |
| 3,840,529 | 10/1974 | Maruyama | 260/240 R |
| 3,843,635 | 10/1971 | Soudijn | 260/240 TC |
| 3,882,109 | 5/1975 | Soudijn | 240/243 A |
| 3,890,323 | 6/1975 | Yamamoto | 260/268 R |
| 3,917,598 | 11/1975 | Maruyama et al. | 260/293.66 |

FOREIGN PATENTS OR APPLICATIONS 2,167,355 8/1973 France

OTHER PUBLICATIONS

Kimura et al., *Chem. Abs.* 62, 11950c, (1964).

*Primary Examiner*—Donald G. Daus
*Assistant Examiner*—Mark L. Berch
*Attorney, Agent, or Firm*—Lawrence S. Levinson; Merle J. Smith; Stephen B. Davis

[57] ABSTRACT

Compounds of the following formula and their acid addition salts

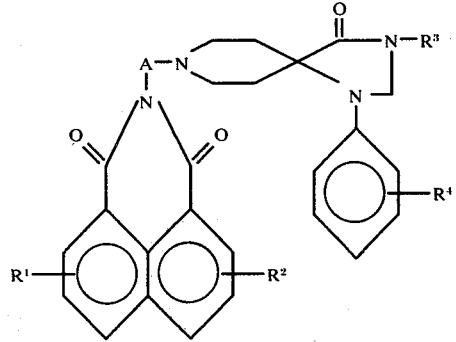

wherein $R^1$ and $R^2$ are selected from hydrogen, lower alkyl, lower alkoxy, lower alkylthio, halogen, trifluoromethyl, amino, nitro and cyano; $R^3$ is hydrogen, lower alkyl or lower alkenyl; $R^4$ is hydrogen, halogen, or lower alkyl; and A is straight or branched chain alkylene are disclosed. These compounds exhibit antidepressant activity. In addition, these compounds are useful as antiinflammatory agents.

13 Claims, No Drawings

2-[(4-OXO-1-PHENYL-1,3,8-TRIAZASPIRO[4.5]DECAN-8-YL)ALKYL]-1H-BENZ[DE]ISOQUINOLIN-1,3(2H)-DIONES

BACKGROUND OF THE INVENTION

Various naphthalimide compounds have been developed for use as dyes and optical brightening agents. Kimura et al. for example, at Chem. Abst., Vol. 62, 11950c, disclose N-[2-piperidinoethyl]-4-methoxy-1,8-naphthalimide (i.e. 6-methoxy-2-[2-(1-piperidinyl)ethyl]-1H-benz[de]isoquinoline-1,3(2H)-dione under the current Chem. Abst. nomenclature) as an optical brightening agent. Noguchi et al. in U.S. Pat. No. 3,625,947 disclose 2-[2-(2- or 4-pyridyl)ethyl]-1H-benz[de]isoquinoline-1,3(2H)-diones as fluorescent whitening agents.

Schenker et al. in U.S. Pat. No. 3,247,208 disclose that 1H-benz[de]isoquinoline-1,3(2H)-diones having a (1-substituted-4-piperidinyl) group in the 2-position possess anesthetic properties. Carron et al. in French Pat. No. 2,167,355 disclose that (4-phenyl)piperidine-2,6-diones having an alkylheteroalkyl substituent at the 1-position possess antidepressant activity. Imides having a nitroimidazolyethyl group as an N-substituent and possessing anti-bacterial and antiprotozoal activity are disclosed in U.S. Pat. Nos. 3,642,836 and 3,770,763 to Cusic et al. Certain imido dicarboxylic acid imides possessing various pharmacological properties are disclosed in U.S. Pat. No. 3,560,495 to Frankus et al.

Pharmaceutically active compounds having a 4-oxo-1-phenyl-1,3,8-triazaspiro[4.5]decan-8yl substituent are disclosed by Janssen in U.S. Pat. Nos. 3,155,670, 3,155,669, 3,161,644, and 3,238,216, by Huebner in U.S. Pat. Nos. 3,759,927 and 3,826,835, by Scharpf et al. in U.S. Pat. No. 3,839,341, by Maruyama in U.S. Pat. No. 3,840,529 and by Soudijn et al. in U.S. Pat. Nos. 3,842,076, 3,843,635, and 3,882,109.

SUMMARY OF THE INVENTION

This invention is directed to new compounds and their pharmaceutically acceptable acid addition salts of the formula

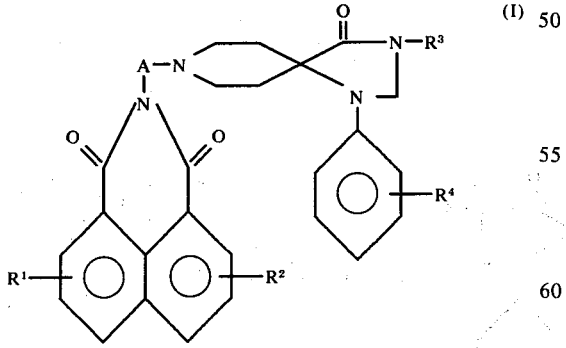

The symbols have the following meaning in formula I and throughout this specification.

$R^1$ and $R^2$ are independently selected from hydrogen, halogen, lower alkyl, lower alkoxy, lower akylthio, trifluoromethyl, nitro, amino and cyano.

$R^3$ is hydrogen, lower alkyl, or lower akenyl.
$R^4$ is hydrogen, lower alkyl, or halogen.
A is straight or branched chain alkylene of 1 to 8 carbons.

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 4 carbons. Examples of the type of groups contemplated are methyl, ethyl, propyl, isopropyl, butyl, etc. The lower alkoxy groups include such lower alkyl groups attached to an oxygen, e.g., methoxy, ethoxy, propoxy, etc. The lower akylthio group include such lower alkyl groups attached to a sulfur, e.g., methylthio, ethylthio, etc.

The lower alkenyl groups referred throughout this specification include straight or branched chain hydrocarbon groups containing 2 to 4 carbons and a single carbon to carbon double bond, i.e. 2-propenyl, 2- or 3-butenyl, 2-methyl-2-propenyl, etc.

The term "halogen" as used throughout this specification refers to fluorine, chlorine, bromine and iodine, with fluorine, chlorine and bromine being preferred and chlorine being most preferred.

Straight or branched chain akylene of 1 to 8 carbons is intended to include groups such as $-(CH_2)_n-$ wherein $n$ is 1 to 8,

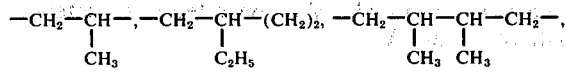

etc.

Preferred compounds of this invention are those having the formula

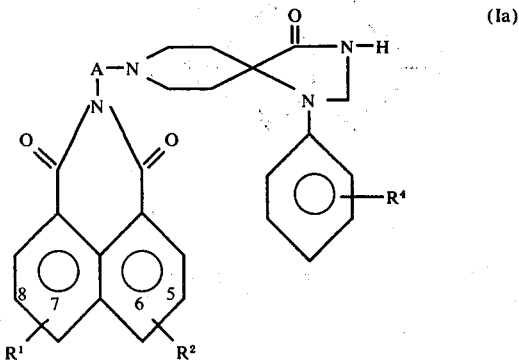

wherein $R^1$ and $R^2$ are independently selected from hydrogen, Cl, Br, F, methyl and methoxy and are located at the 7- or 8-position or 5- or 6-position respectively; $R^4$ is selected from hydrogen, methyl, Cl, Br, and F; and A is straight or branched chain alkylene of 2–6 carbons.

Most preferred are the compounds of formula Ia wherein $R^1$, $R^2$ and $R^4$ are hydrogen and A is straight chain alkylene of 2–6 carbons.

The new compounds of this invention are prepared by the following reactions where A is straight or branched chain alkylene of 2 to 8 carbons.

The substituted naphthalic anhydride of formula II

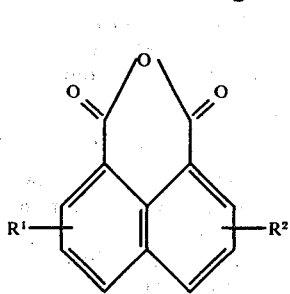

is reacted with an alkanolamine of formula III $H_2N-A-OH$     (III)

to yield the alcohol of formula IV

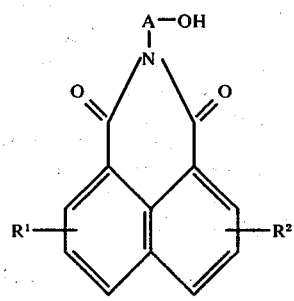

The alcohol of formula IV is converted to the intermediate of formula V

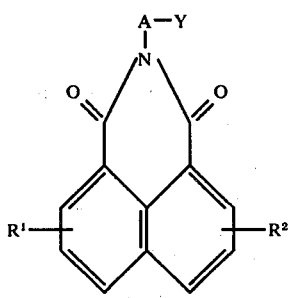

where Y is a leaving group such as tosylate, methanesulfonate or halogen by treating the alcohol with p-toluenesulfonyl chloride, methanesulfonyl chloride, thionyl chloride, thionyl bromide or hydrogen iodide.

The intermediate of formula V is then converted to the final products of formula I by reactions with compounds of the formula VI

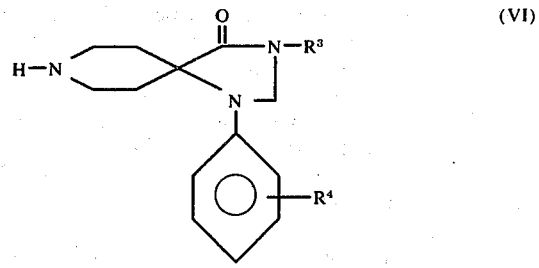

The substituted naphthalic anhydride of formula II can be converted directly to the final products of formula I by reacting the anhydride with compounds of formula VII

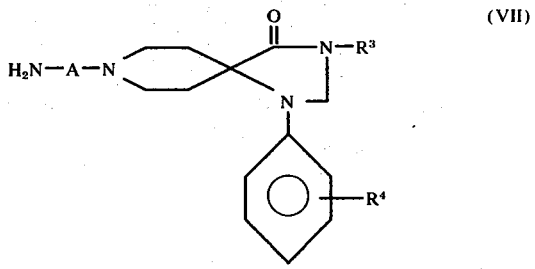

The following schematic summarizes the reactions described above. Where A is straight or branched chain alkylene of 2 to 8 carbons

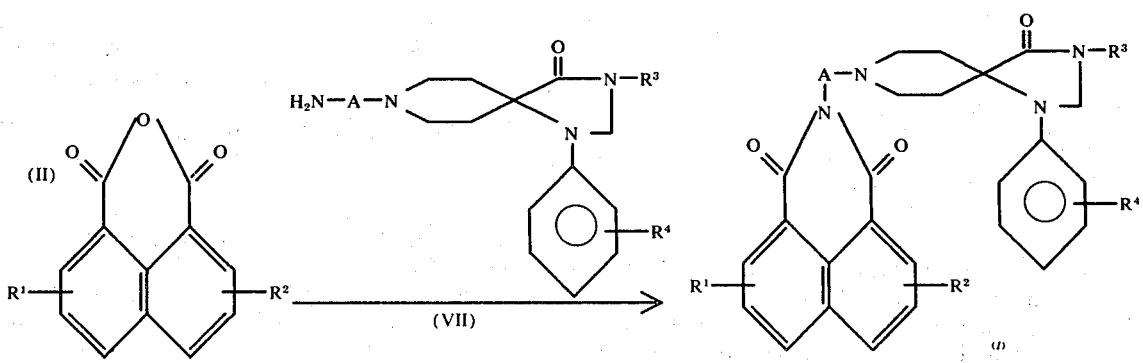

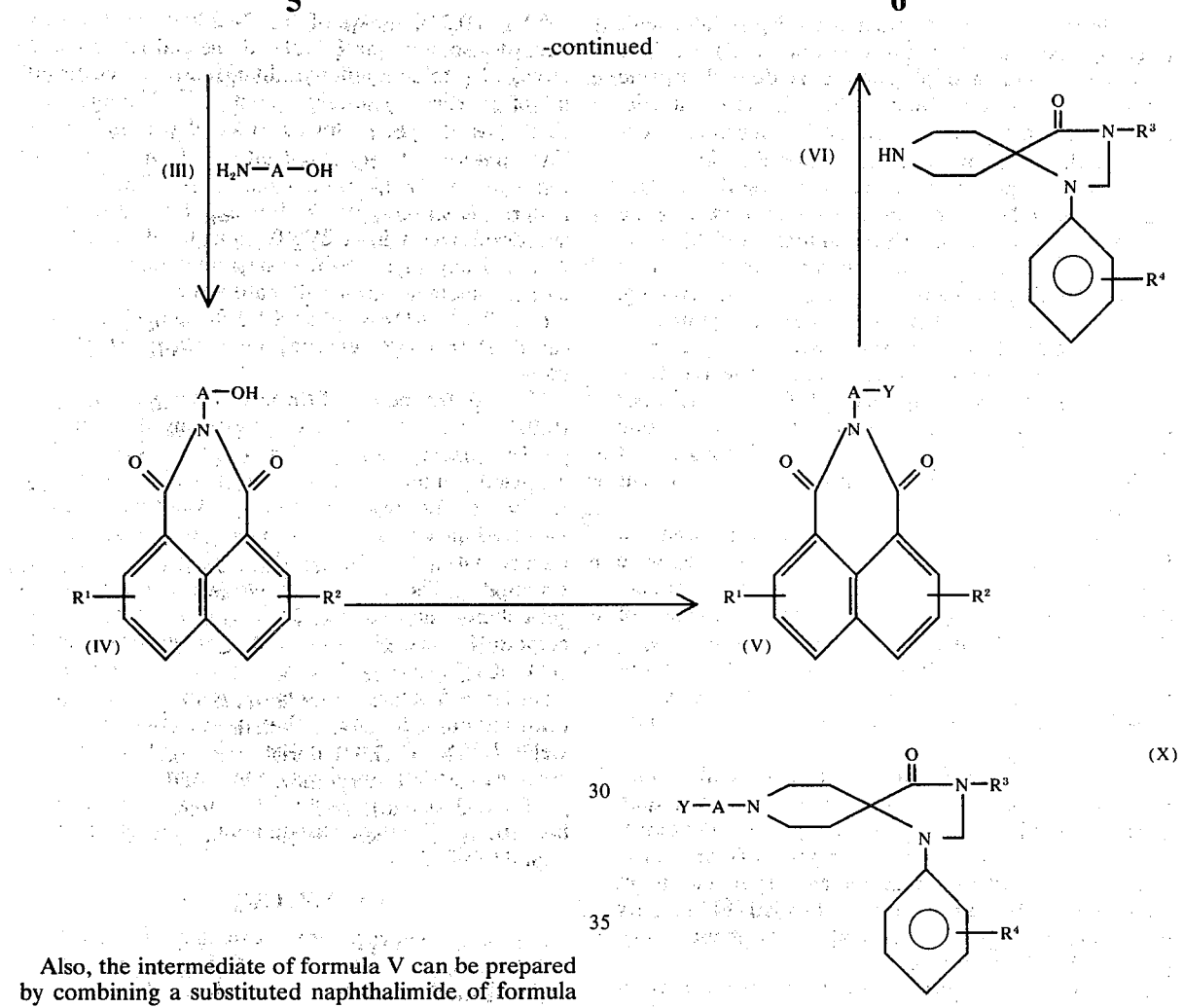

Also, the intermediate of formula V can be prepared by combining a substituted naphthalimide of formula VIII

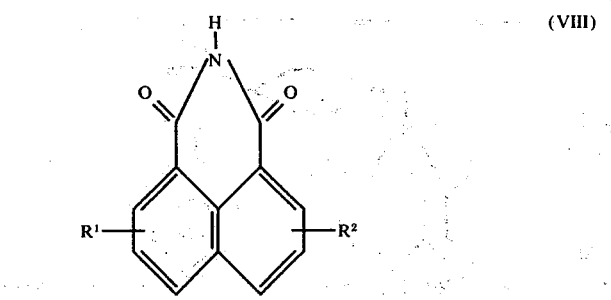

in an organic solvent with a polar organic solvent solution of a base, as for example an alcohol solution of potassium hydroxide, followed by the addition of a solution of the compound of formula IX,

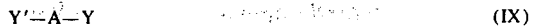

wherein Y' and Y are the same or different and are leaving groups selected from tosylate, methanesulfonate, or halogen and A is a straight or branched chain alkylene of 2 to 8 carbons.

Alternatively, the compounds of formula I wherein A is straight or branched alkylene of 2 to 8 carbons can be prepared by combining the anion of the substituted naphthalimide of formula VIII, described above, with a solution of the compound of formula X, wherein Y is a leaving group as previously defined.

Compounds of formula I where A is —$CH_2$— are prepared by reacting the substituted naphthalimide of formula VIII suspended in a polar organic solvent such as dimethylformamide (DMF) with compounds of the formula VI and a source of formaldehyde such as aqueous formaldehyde or paraformaldehyde.

The various starting materials such as the substituted anhydrides of formula II and the alcohols of formula IV and the substituted naphthalimides of formula VIII are known in the art or are readily obtainable by known procedures. Further process details are also provided in the illustrative examples.

The compounds of formula I wherein either or both of $R^1$ and $R^2$ are amine are prepared by reducing the corresponding nitro substituted compound with a reducing agent such as hydrogen over a palladium catalyst or a suitable chemical reducing agent. This is preferably done as the last stage in the reaction procedures described above.

Depending on the reaction conditions and the starting materials used, the new compounds are obtained in the free form or in the form of their acid addition salts. The salts thereof can be converted into the free compounds in a known manner such as by reaction with a basic agent. Free bases which may be obtained can be converted into pharmaceutically acceptable acid addition salts by reaction with a variety of acids. Acids useful for preparing these acid-addition salts include, inter alia, inorganic acids, such as the hydrohalic acids (e.g. hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic, nicotinic, methanesulfonic or cyclohexanesulfamic.

The new compounds of the present invention including the acid addition salts are capable of modifying the central nervous system. When administered to mice, cats, rats, dogs, and other mammalian species in amounts ranging from about 0.5 mg. to about 100 mg. per kg. of body weight per day, these compounds in particular exhibit antidepressant activity. A preferred dosage regimen for optimum results would be from about 1 mg. to about 5 mg. per kg. of body weight per day, and such dosage units are employed so that a total of from about 35 mg. to about 3 g. of active ingredient in single or divided doses are administered in a 24 hour period.

The antidepressant activity of the compounds of formula I is demonstrated by their ability to antagonize tetrabenazine-induced ptosis according to the procedure of Vernier et al. ("The Pharmacodynamics of Amitriptyline", *Psychosomatic Medicine*, (1962), pages 683–690) and also by their ability to block the reuptake of monoamines in vitro according to the procedure of Horn et al. (*Molecular Pharmacology*, 7th Ed., (1971), page 66).

The compounds of formula I are also useful as anti-inflammatory agents and may be used, for example, in a manner similar to phenylbutazone or indomethacin. They may be used to decrease joint swelling, tenderness, pain and stiffness in mammalian species, e.g., in conditions such as rheumatoid arthritis. The quantity administered ranges from about 1 mg. to about 15 mg. per kg. of body weight per day.

For any of these pharmaceutical purposes a compound or mixture of compounds of formula I or their pharmaceutically acceptable acid addition salts may be administered orally or parenterally in a conventional dosage form such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The following examples are illustrative of the invention and represent preferred embodiments. Other modifications may be readily produced by suitable variations of the reactions. All temperatures are on the centigrade scale.

EXAMPLE 1

2-[2-(4-Oxo-1-phenyl-1,3,8-triazaspiro[4.5]decan-8-yl)ethyl]-1H-benz[de]isoquinoline-1,3(2H)-dione a. 2-(2-Hydroxyethyl)-1H-benz[de]isoquinoline-1,3(2H)-dione 50 g. (0.252 mole) of naphthalic anhydride and 16 g. (0.262 mole) of ethanolamine are refluxed for three hours in 200 ml. of water (the solution is never complete). After cooling to 25° the water is decanted off and the residue recrystallized from 95% ethanol to yield 47.8 g. of 2-(2-hydroxyethyl)-1H-benz[de]isoquinoline-1,3(2H)-dione; m.p. 172°–173°.

b. 2-(2-Hydroxyethyl)-1H-benz[de]isoquinoline-1,3(2H)-dione, 4-methylbenzenesulfonate ester 52 g. (0.216 mole) of the 2-(2-hydroxyethyl)-1H-benz[de]isoquinoline-1,3(2H)-dione and 100 g. (0.525 mole) of p-toluenesulfonyl chloride are added to 600 ml. of pyridine previously cooled to 5°. The mixture is shaken briefly then allowed to stand overnight at 5°. The mixture is then poured into 3000 ml. of ice and water, stirred for 15 minutes and filtered. The insoluble material is stirred with fresh water, filtered off again and dried overnight at 25° (0.1 mm.) yielding 83 g. of 2-(2-hydroxyethyl)-1H-benz[de]isoquinoline-1,3(2H)-dione, 4-methylbenzenesulfonate ester.

c. 2-[2-(4-Oxo-1-phenyl-1,3,8-triazaspiro[4.5]decan-8-yl)ethyl]-1H-benz[de]isoquinoline-1,3(2H)-dione 10 g. (0.025 moles) of the ester from part (b), 6.4 g. (0.027 moles) of 4-oxo-1-phenyl-1,3,8-triazaspiro[4.5]decane, and 3.27 g. (0.25 moles) of diisopropylethylamine are refluxed in 200 ml. of toluene for two hours. The solvent is evaporated and the residue is dissolved in chloroform. The chloroform solution is washed with 10% KOH, washed twice with water, and evaporated. The residue is chromatographed on a silica gel column and eluted with chloroform. Fractions are combined according to TLC (single spot; silica gel:CHCl₃/hexane, 6:4) and the solvent removed to yield 1.5 g. A second run is made using the above quantities and procedure but with dioxane as the solvent and yields 1.25 g. The material from both procedures are combined and recrystallized from ethanol to yield 1.5 g. of 2[2-(4-oxo-1-phenyl-1,3,8-triazaspiro[4.5]decan-8-yl)ethyl]-1H-benz[de]isoquinoline-1,3(2H)-dione; m.p. 236°–237° (dec.).

EXAMPLES 2–12

Following the procedure of example 1 but substituting the alkanolamine shown in Col. I for the ethanolamine the following products are obtained wherein A is the radical shown in Col. II.

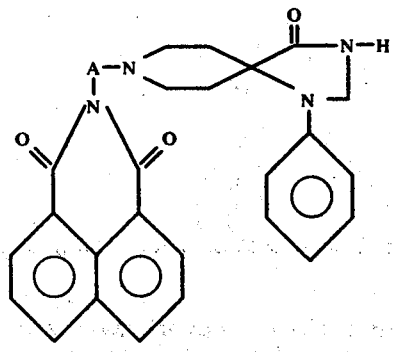

| Ex. | Col. I | Col. II |
| --- | --- | --- |
| 2 | H₂N—(CH₂)₃—OH | —(CH₂)₃— |
| 3 | H₂N—(CH₂)₄—OH | —(CH₂)₄— |
| 4 | H₂N—(CH₂)₅—OH | —(CH₂)₅— |
| 5 | H₂N—(CH₂)₆—OH | —(CH₂)₆— |
| 6 | H₂N—(CH₂)₇—OH | —(CH₂)₇— |
| 7 | H₂N—(CH₂)₈—OH | —(CH₂)₈— |
| 8 | H₂N—CH₂—CH(CH₃)—CH₂—OH | —CH₂—CH(CH₃)—CH₂— |

-continued

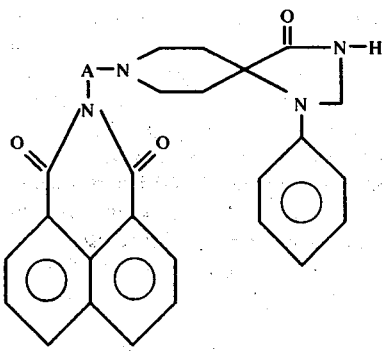

| Ex. | Col. I | Col. II |
|---|---|---|
| 9 | H₂N—CH—(CH₂)₃—OH<br>　　　|<br>　　　CH₃ | —CH—(CH₂)₃—<br>　|<br>　CH₃ |
| 10 | H₂N—(CH₂)₃—CH—OH<br>　　　　　　|<br>　　　　　　CH₃ | —(CH₂)₃—CH—<br>　　　　|<br>　　　　CH₃ |
| 11 | H₂N—CH₂—CH—(CH₂)₂—OH<br>　　　　　|<br>　　　　　C₃H₇ | —CH₂—CH—(CH₂)₂—<br>　　　|<br>　　　C₃H₇ |
| 12 | H₂N—CH—CH₂—CH—OH<br>　　　|　　　　|<br>　　　CH₃　　CH₃ | —CH—CH₂—CH—<br>　|　　　　|<br>　CH₃　　CH₃ |

EXAMPLES 13–25

Following the procedure of example 1 but substituting for the 4-oxo-1-phenyl-1,3,8-triazaspiro[4.5]decane in part (c), one of the following compounds:

4-oxo-1-(2-chlorphenyl)-1,3,8-triazaspiro[4.5]decane;
4-oxo-1-(3-bromophenyl)-1,3,8-triazaspiro[4.5]decane;
4-oxo-1-(4-fluorophenyl)-1,3,8-triazaspiro[4.5]decane;
4-oxo-1-(4-chlorophenyl)-1,3,8-triazaspiro[4.5]decane;
4-oxo-1-(4-iodophenyl)-1,3,8-triazaspiro[4.5]decane;
4-oxo-1-(3-methylphenyl)-1,3,8-triazaspiro[4.5]decane;
4-oxo-1-(4-t-butylphenyl)-1,3,8-triazaspiro[4.5]decane;
3-methyl-4-oxo-1-phenyl-1,3,8-triazaspiro[4.5]decane;
3-ethyl-4-oxo-1-phenyl-1,3,8-triazaspiro[4.5]decane;
3-i-propyl-4-oxo-1-phenyl-1,3,8-triazaspiro[4.5]decane;
3-(2-propenyl)-4-oxo-1-phenyl-1,3,8-triazaspiro[4.5]decane;
3-(2-butenyl)-4-oxo-1-phenyl-1,3,8-triazaspiro[4.5]decane;
and
3-methyl-4-oxo-1-(4-chlorophenyl)-1,3,8-triazaspiro[4.5]-decane
one obtains the following products
2-[2-(4-oxo-1-(2-chlorophenyl)-1,3,8-triazaspiro[4.5]-decan-8-yl)ethyl]-1H-benz[de]isoquinoline-1,3(2H)-dione;
2-[2-(4-oxo-1-(3-bromophenyl)-1,3,8-triazaspiro[4.5]-decan-8-yl)ethyl]-1H-benz[de]isoquinoline-1,3(2H)-dione;
2-[2-(4-oxo-1-(4-fluorophenyl)-1,3,8-triazaspiro[4.5]-decan-8-yl)ethyl]-1H-benz[de]isoquinoline-1,3(2H)-dione;
2-[2-(4-oxo-1-(4-chlorophenyl)-1,3,8-triazaspiro[4.5]-decan-8-yl)ethyl]-1H-benz[de]isoquinoline-1,3(2H)-dione;
2-[2-(4-oxo-(4-iodophenyl)-1,3,8-triazaspiro[4.5]-decan-8-yl)ethyl]-1H-benz[de]isoquinoline-1,3(2H)-dione;
2-[2-(4-oxo-(3-methylphenyl)-1,3,8-triazaspiro[4.5]-decan-8-yl)ethyl]-1H-benz[de]isoquinoline-1,3(2H)-dione;
2-[2-(4-oxo-(4-t-butylphenyl)-1,3,8-triazaspiro[4.5]-decan-8-yl)ethyl]-1H-benz[de]isoquinoline-1,3(2H)-dione:
2-[2-(3-methyl-4-oxo-1-phenyl-1,3,8-triazaspiro[4.5]-decan-8-yl)ethyl]-1H-benz[de]isoquinoline-1,3(2H)-dione;
2-[2-(3-ethyl-4-oxo-1-phenyl-1,3,8-triazaspiro[4.5]-decan-8-yl)ethyl]-1H-benz[de]isoquinoline-1,3(2H)-dione;
2-[2-(4-oxo-1-phenyl-3-i-propyl-1,3,8-triazaspiro[4.5]-decan-8-yl)ethyl]-1H-benz[de]isoquinoline-1,3(2H)-dione;
2-[2-(4-oxo-1-phenyl-3-(2-propenyl)-1,3,8-triazaspiro-[4.5]decan-8-yl)ethyl]-1H-benz[de]isoquinoline-1,3(2H)-dione;
2-[2-(3-(2-butenyl)-4-oxo-1-phenyl-1,3,8-triazaspiro-[4.5]decan-8-yl)ethyl]-1H-benz[de]isoquinoline-1,3(2H)-dione;
and
2-[2-(3-methyl-4-oxo-1-(4-chlorophenyl)-1,3,8-triazaspiro[4.5]decan-8-yl)ethyl]-1H-benz-[de]isoquinoline-1,3(2H)-dione respectively.

Similarly, by employing the alkanolamines of examples 2–12 within the procedure of examples 13–25, other compounds within the scope of the invention are obtained.

EXAMPLE 26

2-[4-(4-oxo-1-phenyl-1,3,8-triazaspiro[4.5]decan-8-yl)butyl]-1H-benz[de]isoquinoline-1,3(2H)-dione, hydrochloride (1:1)

a. 2-(4-Bromobutyl)-1-H-benz[de]isoquinoline-1,3(2H)-dione 100 g. (0.5 mole) of 1,8-naphthalimide is suspended in 2100 ml. of dimethylformamide and the mixture is heated to 90° to form a complete solution. A solution of 36.3 g. (0.55 mole) of potassium hydroxide (85%) in 100 ml. of methanol is added resulting in the immediate formation of a yellow precipitate. The resulting mixture is stirred for one hour at 90° and cooled to 25°. 245 g. (1.0 mole) of 1,4-dibromobutane is added and the mixture is again heated to 90° and stirred for an additional hour. A precipitate remains in the mixture but is more granular than the initial material. The reaction mixture is cooled and the precipitate filtered off. The solvent is removed under vacuum and the residue is diluted with 500 ml. of hexane immediately precipitating crude 2-(4-bromobutyl)-1-H-benz[de]isoquinoline-1,3(2H)-dione. The precipitate is filtered off, washed with fresh hexane and dried for 2 hours at 50° (0.1 mm.) to yield 2-(4-bromobutyl)-1-H-benz[de]isoquinoline-1,3(2H)-dione. An analytically pure sample is prepared by dissolving the above product in hot 95% ethanol and recrystallizing by allowing the solution to cool to 25°. The resulting precipitate is dried for two hours at 50° (0.1 mm.) to yield pure 2-(4-bromobutyl)-1H-benz[de]isoquinoline-1,3(2H)-dione; m.p. 113°-115°.

b. 2-[4-(4-Oxo-1-phenyl-1,3,8-triazaspiro[4.5]decan-8-yl)butyl]-1H-benz[de]isoquinoline-1,3(2H)-dione, hydrochloride (1:1)

10 g. (0.03 moles) of the bromide from part (a) and 7.6 g. (0.03 moles) of 4-oxo-1-phenyl-1,3,8-triazaspiro[4.5]decane are refluxed over excess (10 g.) sodium carbonate in 250 ml. of n-butanol overnight. The butanol is evaporated and the residue is taken up overnight. The aqueous layer is washed with chloroform. The chloroform layers are combined, washed twice with water, filtered, and evaporated. The residue is taken up in 800 ml. of hot ethanol, filtered hot to remove a small amount of insoluble material, and 5 ml. of concentrated HCl is added to precipitate 11.9 g. of 2-[4-(4-oxo-1-phenyl-1,3,8-triazaspiro[4.5]decan-8-yl)butyl]-1H-benz[de]isoquinoline-1,3(2H)-dione hydrochloride (1:1); m.p. 277°-279°.

EXAMPLE 27

2-[5-(4-Oxo-1-phenyl-1,3,8-triazaspiro[4.5]decan-8-yl)pentyl]-1H-benz[de]isoquinoline-1,3(2H)-dione, hydrochloride (1:1)

a. 2-(5-Bromobutyl)-1H-benz[de]isoquinoline-1,3(2H)-dione

Following the procedure of part (a) of example 26 but substituting 1,5-dibromopentate for the 1,4-dibromobutane, one obtains 2-(5-bromopentyl)-1H-benz[de]isoquinoline-1,3(2H)-dione; m.p. 113°-115°.

b. 2-[5-(4-Oxo1-phenyl-1,3,8-triazaspiro[4.5]decan-8-yl)pentyl]-1H-benz[de]isoquinoline-1,3(2H)-dione, hydrochloride (1:1)

Following the procedure of part (b) of example 26 but substituting 2-(5-bromopentyl)-1H-benz[de]isoquinoline-1,3(2H)-dione for the 2-(4-bromobutyl)-1H-benz[de]isoquinoline-1,3(2H)-dione, one obtains the titled compound.

EXAMPLE 28

2-[6-(4-Oxo-1-phenyl-1,3,8-triazaspiro[4.5]decan-8-yl)hexyl]-1H-benz[de]isoquinoline-1,3(2H)-dione, hydrochloride (1:1)

a. 2-(6-Bromohexyl)-1H-benz[de]isoquinoline-1,3(2H)-dione

Following the procedure of part (a) of example 26 but substituting 1,6-dibromohexane for the 1,4-dibromobutane, one obtains 2-(6-bromohexyl)-1H-benz[de]isoquinoline-1,3(2H)-dione; m.p. 95°-96°.

b. 2-[6-(4-Oxo-1-phenyl-1,3,8-triazaspiro[4.5]decan-8yl)hexyl]-1H-benz[de]isoquinoline-1,3(2H)-dione, hydrochloride (1:1)

Following the procedure of part (b) of example 26 but substituting 2-(6-bromohexyl)-1H-benz[de]isoquinoline-1,3(2H)-dione for the 2-(4-bromobutyl)-1H-benz[de]isoquinoline-1,3-(2H)-dione, one obtains the titled compound.

Alternatively, the procedure of examples 26–28 can be employed to prepare the compounds of examples 1–25.

EXAMPLE 29

2-[(4-Oxo-1-phenyl-1,3,8-triazaspiro[4.5]decan-8-yl)methyl]-1H-benz[de]isoquinoline-1,3(2H)-dione An equimolar mixture of 4-oxo-1-phenyl-1,3,8-triazaspiro-[4.5]decane, aqueous formaldehyde, and 1,8-naphthalimide is suspended in a small amount of dimethylformamide and the mixture is heated until dissolution is complete. The solution is allowed to stand at room temperature and the resulting precipitate is filtered off and dried to yield the titled compound.

Similarly, by employing the triazaspiro[4.5]decanes of examples 13–25 within the procedure of example 29, other compounds within the scope of the invention are obtained.

EXAMPLES 30–55

Following the procedure of example 1 but substituting for the 2-(2-hydroxyethyl)-1H-benz[de]isoquinoline-1,3(2H)-dione, 4-methylbenzenesulfonate ester the ester shown in Col. I one obtains the product in Col. II.

| Col. I | Col. II |
|---|---|
| 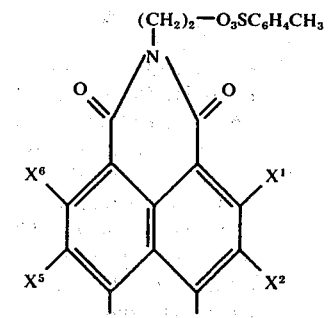 | 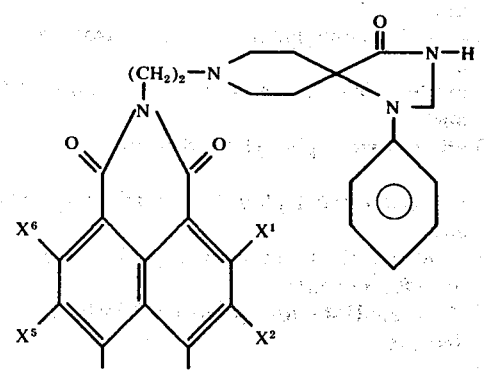 |

| Ex. | X¹ | X² | X³ | X⁴ | X⁵ | X⁶ |
|---|---|---|---|---|---|---|
| 30 | H | H | Br | H | H | H |
| 31 | H | Cl | H | H | H | H |
| 32 | H | Br | H | H | H | H |
| 33 | H | F | H | H | H | H |
| 34 | H | I | H | H | H | H |

-continued

| Ex. | X¹ | X² | X³ | X⁴ | X⁵ | X⁶ |
|---|---|---|---|---|---|---|
| 35 | H | Cl | H | H | Cl | H |
| 36 | Br | H | H | H | H | H |
| 37 | H | H | Cl | Cl | H | H |
| 38 | H | H | $CH_3$ | H | H | H |
| 39 | H | H | $C_2H_5$ | H | H | H |
| 40 | H | H | $i$-$C_3H_7$ | H | H | H |
| 41 | H | H | $CH_3$ | $CH_3$ | H | H |
| 42 | H | H | $OCH_3$ | H | H | H |
| 43 | H | H | $OC_2H_5$ | H | H | H |
| 44 | H | H | $OC_3H_7$ | H | H | H |
| 45 | H | H | $OCH_3$ | $OCH_3$ | H | H |
| 46 | H | $NO_2$ | H | H | H | H |
| 47 | H | H | $NO_2$ | H | H | H |
| 48 | H | $CF_3$ | H | H | H | H |
| 49 | H | H | $CF_3$ | H | H | H |
| 50 | H | CN | H | H | H | H |
| 51 | H | H | CN | H | H | H |
| 52 | H | H | $NH_2$ | H | H | H |
| 53 | H | $NH_2$ | H | H | H | H |
| 54 | H | $SC_3H_7$ | H | H | H | H |
| 55 | H | H | $SCH_3$ | H | H | H |

Similarly, by employing the ester of Col. I of examples 30–55 in the procedure of examples 13 to 25, other compounds within the scope of this invention are prepared.

Similarly, by following the procedure of examples 2–12, but employing a substituted 1,8-naphthalic anhydride of formula II wherein the substituents are those listed under the headings X¹, X², X³, X⁴, X⁵, and X⁶ in exaples 30–55, other compounds within the scope of the invention are prepared. Also, by following the procedures of examples 26–29 but employing a substituted 1,8-naphthalimide of formula VIII wherein the substituents are those listed under the headings X¹, X², X³, X⁴, X⁵, and X⁶ in examples 30 to 55, other compounds within the scope of this invention are prepared.

What is claimed is:
1. A compound of the formula

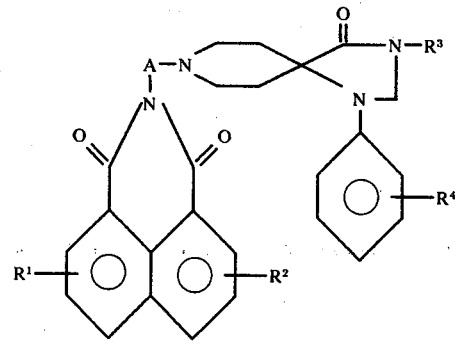

wherein $R^1$ and $R^2$ are independently selected from the group consisting of hydrogen, lower alkyl, lower alkoxy, lower alkylthio, halogen, trifluoromethyl, amino, nitro and cyano; $R^3$ is selected from the group consisting of hydrogen, lower alkyl and lower alkenyl; $R^4$ is selected from the group consisting of hydrogen, lower alkyl, and halogen, and A is a straight or branched chain alkylene of 1 to 8 carbons; and a pharmaceutically acceptable acid addition salt thereof.

2. The compound of claim 1 wherein A is straight or branched chain alkylene of 2 to 6 carbons.

3. The compound of claim 1 having the formula

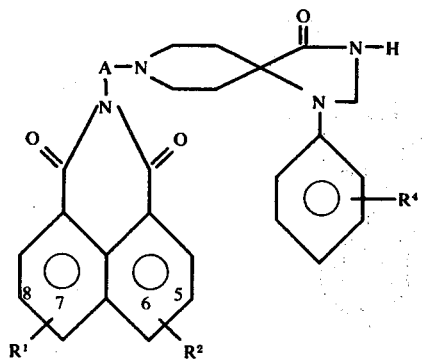

wherein R[1] is located at either the 7- or 8-position and R[2] is located at either the 5- or 6-position and R[1] and R[2] are independently selected from the group consisting of hydrogen, Cl, Br, F, methyl and methoxy; R[4] is selected from the group consisting of hydrogen, methyl, Cl, Br and F; and A is straight or branched chain alkylene of 1 to 6 carbons; and a pharmaceutically acceptable salt thereof.

4. The compound of claim 3 wherein A is straight or branched chain alkylene of 2 to 6 carbons.

5. The compound of claim 4 wherein R[1], R[2] and R[4] are hydrogen; and A is straight chain alkylene of 2 to 6 carbons.

6. The compound of claim 5 wherein A is

—(CH$_2$)$_2$—

7. The compound of claim 5 wherein A is

—(CH$_2$)$_3$—.

8. The compound of claim 5 wherein A is

—(CH$_2$)$_4$—.

9. The compound of claim 8 having the name 2-[4-(4-oxo-1-phenyl-1,3,8-triazaspiro[4.5]decan-8-yl)butyl]-1H-benz[de]isoquinoline-1,3(2H)-dione, hydrochloride (1:1).

10. The compound of claim 5 wherein A is

—(CH$_2$)$_5$—.

11. The compound of claim 5 wherein A is

—(CH$_2$)$_6$—.

12. A composition useful for treating depression in mammals comprising as the active ingredients from about 0.5 to about 100 mg. per kg. of body weight of the mammal being treated of a compound or mixtures of compounds of claim 1 and a pharmaceutically acceptable carrier.

13. The method of treating depression in mammals comprising administering an effect amount of the composition of claim 12.

* * * * *

UNITED STATES PATENT AND TRADEMARK OFFICE
CERTIFICATE OF CORRECTION

PATENT NO. : 3,996,363
DATED : December 7, 1976
INVENTOR(S) : Wade et al.

It is certified that error appears in the above-identified patent and that said Letters Patent are hereby corrected as shown below:

Col. 1, line 37, "8yl" should read --8-yl--.

Col. 2, line 1, "akenyl" should read --alkenyl--.

Col. 2, line 28, "akylene" should read --alkylene--.

Col. 8, line 31, "2[2" should read --2-[2--.

Col. 10, line 48, "1-H" should read --1H--.

Col. 10, line 64, "1-H" should read --1H--.

Col. 10, line 67, "1-H" should read --1H--.

Col. 11, lines 14 and 15, "overnight" should be deleted and in its place should read --in chloroform and water--.

Col. 11, line 32, "dibromopentate" should read --dibromopentane--.

Col. 11, line 35, "Oxol" should read --Oxo-1--.

Col. 12, line 13, "8yl" should read --8-yl--.

Col. 13, line 59, "exaples" should read --examples--.

Signed and Sealed this

Third Day of May 1977

[SEAL]

Attest:

RUTH C. MASON
*Attesting Officer*

C. MARSHALL DANN
*Commissioner of Patents and Trademarks*